United States Patent
Fox et al.

(10) Patent No.: US 9,259,331 B2
(45) Date of Patent: Feb. 16, 2016

(54) SPRING LOADED ADJUSTABLE JOINT SPACER/BEARING TRIAL SYSTEM

(71) Applicant: Biomet Manufacturing, LLC, Warsaw, IN (US)

(72) Inventors: Duke Fox, Warsaw, IN (US); Preston Lee Howard, Wolcottville, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 44 days.

(21) Appl. No.: 14/195,156

(22) Filed: Mar. 3, 2014

(65) Prior Publication Data

US 2014/0277543 A1 Sep. 18, 2014

Related U.S. Application Data

(60) Provisional application No. 61/791,302, filed on Mar. 15, 2013.

(51) Int. Cl.
*A61F 2/30* (2006.01)
*A61F 2/38* (2006.01)
*A61F 2/46* (2006.01)

(52) U.S. Cl.
CPC .............. *A61F 2/4684* (2013.01); *A61F 2/38* (2013.01); *A61F 2002/30556* (2013.01); *A61F 2002/30565* (2013.01)

(58) Field of Classification Search
CPC ...... A61F 2/389; A61F 2/3868; A61F 2/4611; A61F 2/442; A61F 2/28; A61F 2/4684
See application file for complete search history.

(56) References Cited

U.S. PATENT DOCUMENTS

| | | | |
|---|---|---|---|
| 7,455,647 B2 | 11/2008 | Tarabichi | |
| 7,892,285 B2 | 2/2011 | Viker | |
| 2010/0030335 A1 | 2/2010 | Arramon | |
| 2011/0046744 A1* | 2/2011 | Errico et al. | 623/17.16 |
| 2011/0060422 A1* | 3/2011 | Makower et al. | 623/46 |
| 2011/0071636 A1 | 3/2011 | Tsuang et al. | |
| 2011/0118845 A1* | 5/2011 | Overes et al. | 623/17.16 |

* cited by examiner

*Primary Examiner* — Jason-Dennis Stewart
(74) *Attorney, Agent, or Firm* — Schwegman Lundberg & Woessner, P.A.

(57) ABSTRACT

A joint spacer for an orthopedic procedure including a first plate, a second plate, a coupling device, and a spacer insert receiving portion. The first plate includes a first bone facing surface and a first inner surface. The second plate includes a second bone facing surface and a second inner surface facing the first inner surface. The coupling device couples the first plate and the second plate together. The spacer insert receiving portion of at least one of the first inner surface or the second inner surface is configured to receive at least one spacer insert between the first plate and the second plate to space the first plate and the second plate apart a distance corresponding to an optimal interval between bones of a joint.

22 Claims, 10 Drawing Sheets

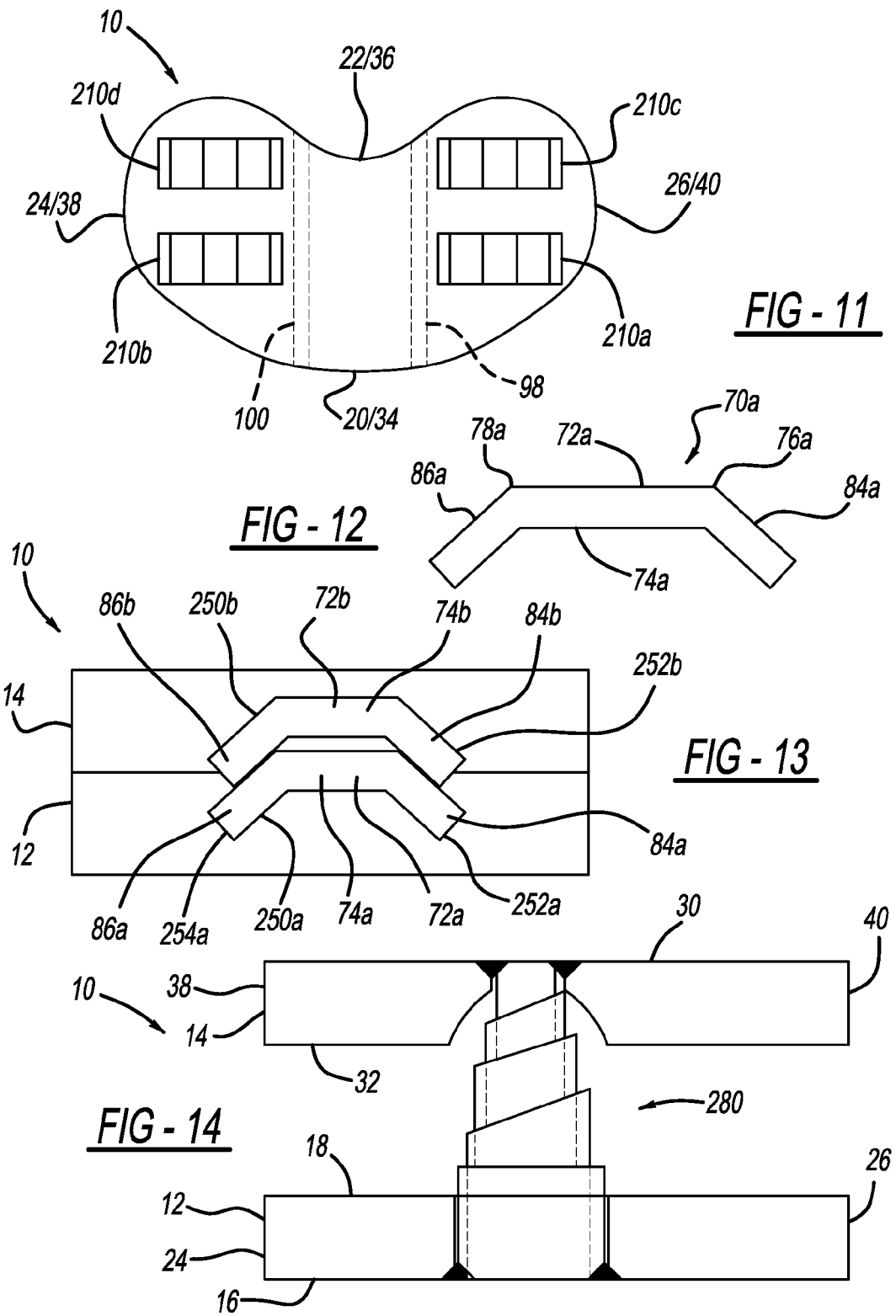

SPRING LOADED ADJUSTABLE JOINT SPACER/BEARING TRIAL SYSTEM

CROSS-REFERENCE TO RELATED APPLICATION

This application claims the benefit of U.S. Provisional Application No. 61/791,302 filed on Mar. 15, 2013, the entire disclosure of which is incorporated herein by reference.

FIELD

The present disclosure relates to a spring-loaded adjustable joint spacer and bearing trial system.

BACKGROUND

This section provides background information related to the present disclosure, which is not necessarily prior art.

During a total knee arthroplasty, some orthopedic surgeons prefer to balance the flexion and extension gaps with a gap spacer. This typically involves inserting individual spacers of different thicknesses one spacer at a time until the ligaments are properly tensed. An individual spacer must thus be removed and replaced each time an adjustment of the flexion/extension gaps is desired. Some systems include a single primary spacer block and a plurality of shims that can be added to the block to increase the overall thickness of the primary block. To make an adjustment, the primary spacer block must be removed and shims must be either added or removed from the primary spacer block. With both systems, the spacer must be undesirably removed from the joint for the flexion/extension gap to be adjusted.

After the femur and tibia have been prepared, the surgeon must determine the thickness of the tibial bearing insert to be implanted. Tibial bearing trial systems typically include a tibial trial and a plurality of bearing inserts of different thicknesses, which can be selectively coupled to the tibial trial. The bearing inserts must be individually inserted into the joint space and coupled to the tibial trial until the bearing of the desired thickness is identified.

A joint spacer and bearing trial that can be provided with different thicknesses without having to remove the spacer from the joint space would thus be desirable.

SUMMARY

This section provides a general summary of the disclosure, and is not a comprehensive disclosure of its full scope or all of its features.

The present teachings provide for a joint spacer for an orthopedic procedure including a first plate, a second plate, a coupling device, and a spacer insert receiving portion. The first plate includes a first bone facing surface and a first inner surface. The second plate includes a second bone facing surface and a second inner surface facing the first inner surface. The coupling device couples the first plate and the second plate together. The spacer insert receiving portion of at least one of the first inner surface or the second inner surface is configured to receive at least one spacer insert between the first plate and the second plate to space the first plate and the second plate apart a distance corresponding to an optimal interval between bones of a joint.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 11 is a plan view of a trial joint spacer according to the present teachings;

FIG. 12 is a side view of a spacer insert according to the present teachings;

FIG. 13 is a side view of a joint spacer according to the present teachings with two spacer inserts according to FIG. 12 coupled thereto;

FIG. 14 is a side view of another coupling device for the trial joint spacer according to the present teachings;

Corresponding reference numerals indicate corresponding parts throughout the several views of the drawings.

DETAILED DESCRIPTION

Example embodiments will now be described more fully with reference to the accompanying drawings.

Figure 1:
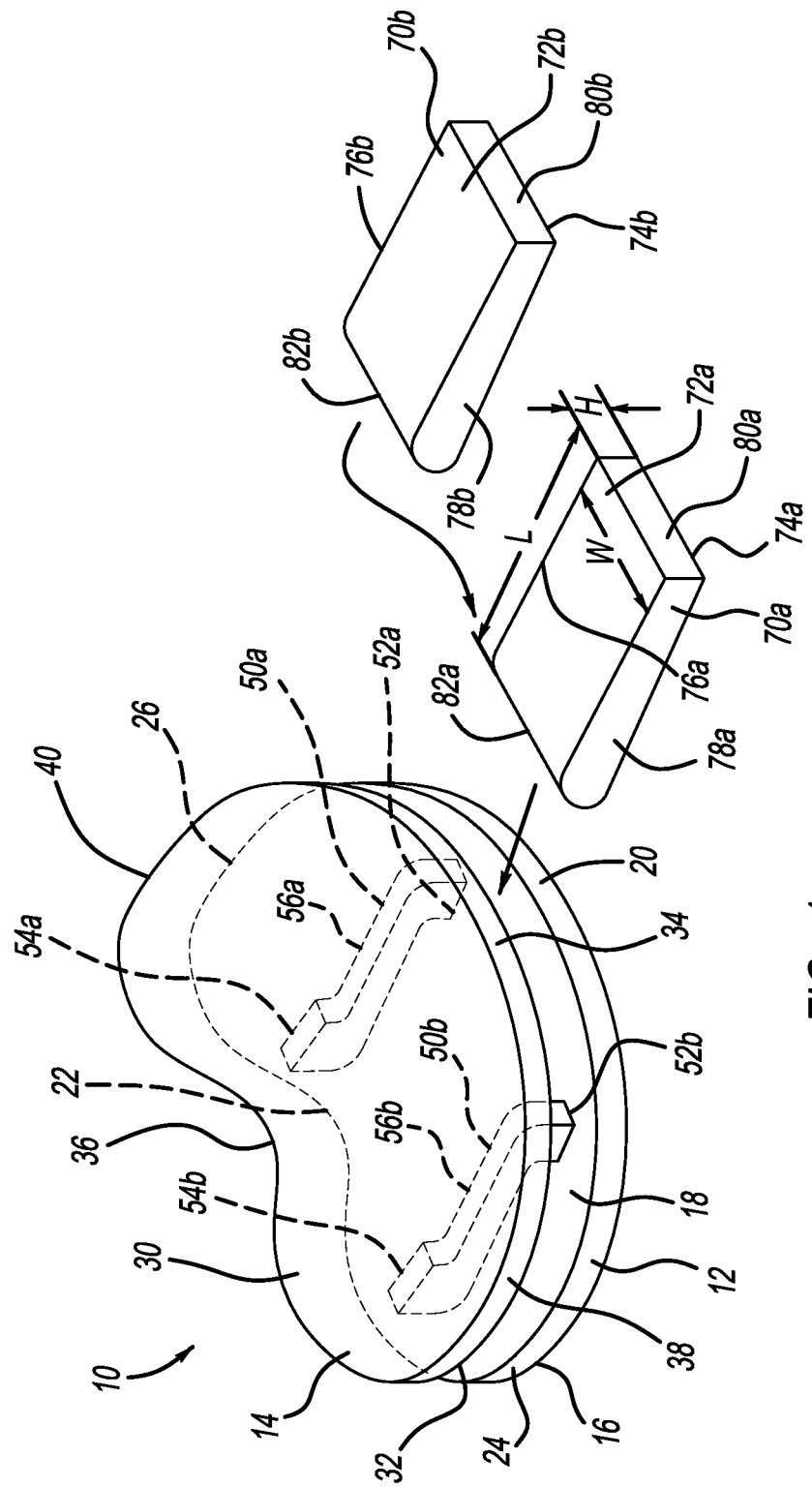
FIG. 1 is a perspective view of a trial joint spacer according to the present teachings.

With initial reference to FIG. 1, a trial joint spacer according to the present teachings is generally illustrated at reference numeral 10. Although the joint spacer 10 is described herein as a knee joint spacer for insertion between a femur and tibia in order to assess flexion and extension gaps therebetween, the present teachings can be applied to joint spacers for use at any joint, and thus the joint spacer 10 can be shaped, sized and/or configured for use at any suitable joint.

The joint spacer 10 generally includes a first plate 12 and a second plate 14. The first plate 12 includes a first bone facing surface 16, such as for facing a bone surface of a tibia bone. Opposite to the first bone facing surface 16 is a first inner surface 18 of the first plate 12. The first plate 12 includes an anterior side 20 and a posterior side 22, which is opposite to the anterior side 20. Between the anterior side 20 and the posterior side 22 is a medial side 24 and a lateral side 26. The medial side 24 is opposite to the lateral side 26. The references to the medial side 24, lateral side 26, anterior side 20, and posterior side 22 herein are for reference purposes only, and one skilled in the art will realize that the lateral side 26 can be the medial side 24 and the medial side 24 can be the lateral side 26 depending on whether the joint spacer 10 is configured for use in a right or left knee.

The second plate 14 includes a second bone facing surface 30, such as for facing the tibia bone. Opposite to the second bone facing surface 30 is a second inner surface 32. The second inner surface 32 is arranged opposite to and faces the first inner surface 18.

The second plate 14 includes an anterior side 34 and a posterior side 36, which is opposite to the anterior side 34. A medial side 38 of the second plate 14 is opposite to a lateral side 40 of the second plate 14. Reference to the medial side 38 and the lateral side 40 is for ease of discussion only and will depend on which leg the joint spacer 10 is configured for use with, as one skilled in the art will appreciate. Therefore, the medial side 38 can be the lateral side 40 and the lateral side 40 can be the medial side 38.

The first plate 12 and the second plate 14 are coupled together with any suitable coupling device, such as with any resilient device or spring. As illustrated in FIG. 1, the coupling device includes a first coupling device 50a and a second coupling device 50b. The first coupling device 50a is arranged proximate to the lateral side 26, and includes a first end 52a and a second end 54a. The first end 52a is coupled to the first plate 12 proximate to the anterior side 20. The second end 54a is coupled to the second plate 14 proximate to the posterior side 36. Extending between the first end 52a and the second end 54a is an intermediate or elongated portion 56a. The elongated portion 56a thus generally extends between the anterior sides 20 and 34, and the posterior sides 22 and 36. The elongated portion 56a is spaced apart from the first plate 12 and the second plate 14 by the first and second ends 52a and 54a thereof. The second coupling device 50b is similar to the first coupling device 50a, and thus is illustrated using the same reference numbers as used to illustrate the first coupling device 50a, but with the suffix "b." The second coupling device 50b is proximate to the medial side 24 of the first plate 12 and the medial side 38 of the second plate 14. The second coupling device 50b is arranged such that the elongated portion 56b extends generally parallel to the elongated portion 56a of the first coupling device 50a.

The first and second coupling devices 50a and 50b are spaced apart in order to accommodate one or more spacer inserts 70 therebetween. FIG. 1 illustrates a first spacer insert 70a and a second spacer insert 70b. The spacer insert 70a includes a top surface 72a and a bottom surface 74a opposite thereto. A first side surface 76a is opposite to a second side surface 78a, and an anterior surface 80a is opposite to a posterior surface 82a. The spacer insert 70a can be provided with any suitable height H, length L, and width W. Insertion of the insert 70a between the first plate 12 and the second plate 14 will space the first and second plates 12 and 14 apart at a distance approximately equal to the height H of the first spacer insert 70a. The second spacer insert 70b is illustrated as being substantially similar to the first spacer insert 70a, and thus like features are designated with the same reference numbers, but include the suffix "b."

The first spacer insert 70a can be inserted between the first and second plates 12 and 14 such that the bottom surface 74a abuts the first inner surface 18 of the first plate 12, and the top surface 72a abuts the second inner surface 32 of the second plate 14. The first inner surface 18 and the second inner surface 32 thus at least partially define a spacer insert receiving portion of the joint spacer 10.

Any suitable number of the spacer inserts 70 can be provided, and the spacer inserts 70 can include any suitable size, shape or configuration to space the first plate 12 and the second plate 14 apart at desired distance. The spacer inserts 70 can include any suitable indicia or marking thereon to identify to a surgeon the distance that each individual spacer insert 70, such as first and second spacer inserts 70a and 70b, will space the first and second plates 12 and 14 apart. Indicia can also be provided to inform the surgeon of the height or thickness that the joint spacer 10 will be provided with as measured between the first bone facing surface 16 and the second bone facing surface 30 upon insertion any one or more of the spacer inserts 70 therebetween.

Multiple spacer inserts 70 can be arranged between the first plate 12 and the second plate 14 in any suitable manner. For example, the first spacer insert 70a can be seated on the first inner surface 18 and the second spacer insert 70b can be seated upon the top surface 72a of the first spacer insert 70a. The top surface 72b of the second spacer insert 70b can thus be arranged to contact the second inner surface 32 of the second plate 14.

Figure 2:
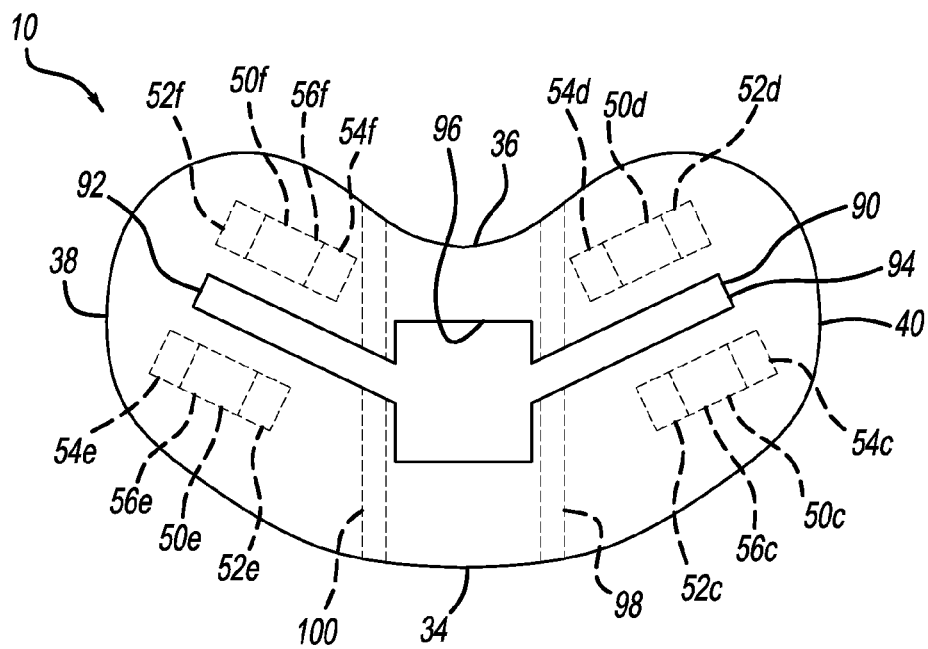
FIG. 2 is a plan view of a plate of the trial joint spacer according to the present teachings.

With additional reference to FIG. 2, the joint spacer 10 can be provided with coupling devices that extend generally in the medial to lateral direction, rather than in the anterior/posterior direction illustrated in FIG. 1 with respect to the first and second coupling devices 50a and 50b. For example, and as illustrated in FIG. 2, the joint spacer 10 can include a third coupling device 50c, a fourth coupling device 50d, a fifth coupling device 50e, and a sixth coupling device 50f. The coupling devices 50c-50f are each generally similar to the first and second coupling devices 50a and 50b, but for their orientation on the joint spacer 10. Therefore, the reference numbers used to describe the first and second coupling devices 50a and 50b will be used to describe and illustrate the third through sixth coupling devices 50c-50f, but with different alphanumeric suffixes. The coupling devices 50c-50f can generally be resilient members, such as springs.

With continued reference to FIG. 2 and additional reference to FIG. 3, the specific orientation and arrangement of each one of the third through sixth coupling devices 50c-50f will now be described. The third coupling device 50c is arranged such that its first end 52c is coupled to the first plate 12, and its second end 54c is coupled to the second plate 14. The second end 54c is closer to the lateral side 40 of the second plate 14 than the first end 52 is to the lateral side 26 of the second plate 14. The third coupling device 50c is proximate to the anterior sides 20 and 34 of the first and second plates 12 and 14 respectively.

The fourth coupling device 50d is proximate to the lateral sides 26 and 40, and proximate to the posterior sides 22 and 36. The first end 52d is mounted to the first plate 12 and the second end 54d is mounted to the second plate 14. The first end 52d is closer to the lateral side 26 of the first plate 12 than the second end 54d is to the lateral side 40 of the second plate 14. The third and fourth coupling devices 50c and 50d are thus generally arranged in opposite directions.

The fifth coupling device 50e is at the medial side 24 and 38 of the first and second plates 12 and 14 respectively, and proximate to the anterior sides 20 and 34. The first end 52e is coupled to the first plate 12 and the second end 54e is coupled to the second plate 14. The second end 54e is closer to the medial sides 24 and 38 than the first end 52e is.

The sixth spring 50f is arranged at the medial sides 24 and 38 proximate to the posterior sides 22 and 36. The first end 52f is mounted to the first plate 12 and the second end 54f is mounted to the second plate 14. The first end 52f is closer to the medial sides 24 and 38 than the second end 54f is. The fifth and sixth coupling devices 50e and 50f are thus arranged in opposite directions.

The second plate 14 defines a slot 90 at the second bone facing surface 30. The slot 90 can be a recess within the second bone facing surface 30, or can extend completely through the second plate 14 from the second bone facing surface 30 to the second inner surface 32. The slot 90 extends generally between the medial side 38 and the lateral side 40. The slot 90 includes a first end 92 proximate to the medial side 38, and a second end 94 proximate to the lateral side 40. The slot 90 is generally configured and arranged to couple a trial bearing plate 150 (described herein and illustrated at FIGS. 4 and 5) to the second plate 14 at the second bone facing surface 30 to provide a trial bearing surface for the femoral condyles.

The second plate 14 further defines a first aperture 96 extending through the second plate 14 approximately equidistant between the medial side 38 and the lateral side 40. The first aperture 96 is aligned with a second aperture (not shown) defined by the first plate 12. The first aperture 96 is substantially similar to the second aperture vertically aligned therewith. The first aperture 96 and the second aperture can be configured to receive, for example, a bone punch therethrough for preparing the tibia bone to couple with a tibial tray.

Figure 3:
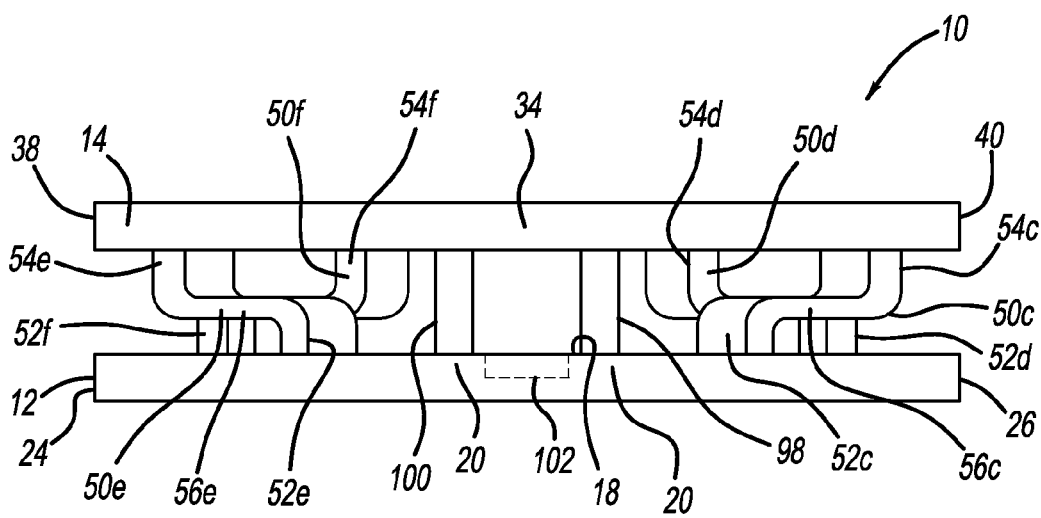
FIG. 3 is a side view of a trial joint spacer according to the present teachings.

The joint spacer 10 of FIGS. 2 and 3 further includes a first stop or rail 98 and a second stop or rail 100. The first and second stops 98 and 100 are arranged at any suitable position between the first and second plates 12 and 14 to maintain a minimum separation distance between the first and second plates 12 and 14 generally equal to a height of the first and second stops 98 and 100. The first and second stops 98 and 100 can be fixably mounted to the first inner surface 18 of the first plate 12 for example.

As illustrated in FIG. 3, the joint spacer 10 defines a guide, slot, or track 102 at the first inner surface 18 of the first plate 12. The guide can have any suitable configuration, size, and/or shape to cooperate with any portion of the spacer inserts 70, such as a flange extending from the spacer insert 70a in order to guide the spacer insert 70a to an appropriate position between the first and second plates 12 and 14, such as at the first inner surface 18. The guide 102 is arranged to generally center the spacer inserts 70 between the lateral sides 26/40 and the medial sides 24/38.

Figure 4:
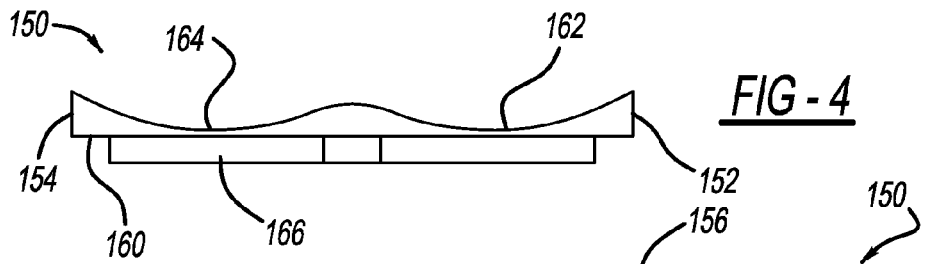
FIG. 4 is as side view of a trial bearing plate according to the present teachings.
Figure 5:
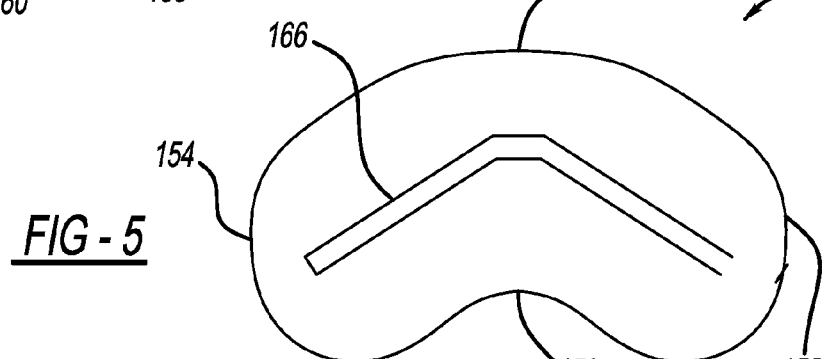
FIG. 5 is a plan view of the trial bearing plate of FIG. 4.

With reference to FIGS. 4 and 5, the trial bearing plate 150 will be described further. The trial bearing plate 150 includes a medial side 152 and a lateral side 154, which are identified for ease of reference only and can be reversed depending on whether the trial bearing plate 150 is configured to articulate with the right or left femur. The trial bearing plate 150 further includes an anterior side 156 and a posterior side 158, which is opposite to the anterior side 156. An undersurface 160 of the trial bearing plate 150 is opposite to bearing surfaces thereof, such as a medial condyle bearing surface 162 and a lateral condyle bearing surface 164. At the undersurface 160 is a flange 166, which extends between the medial side 152 and the lateral side 154. The flange 166 is sized and shaped for receipt within the slot 90 (FIG. 2) of the second plate 14. The trial bearing plate 150 may be seated on the second bone facing surface 130 of the second plate 14 and be retained at the second bone facing surface 30 to provide trial articulation surfaces for the medial and lateral condyles of the femur.

Figure 6:
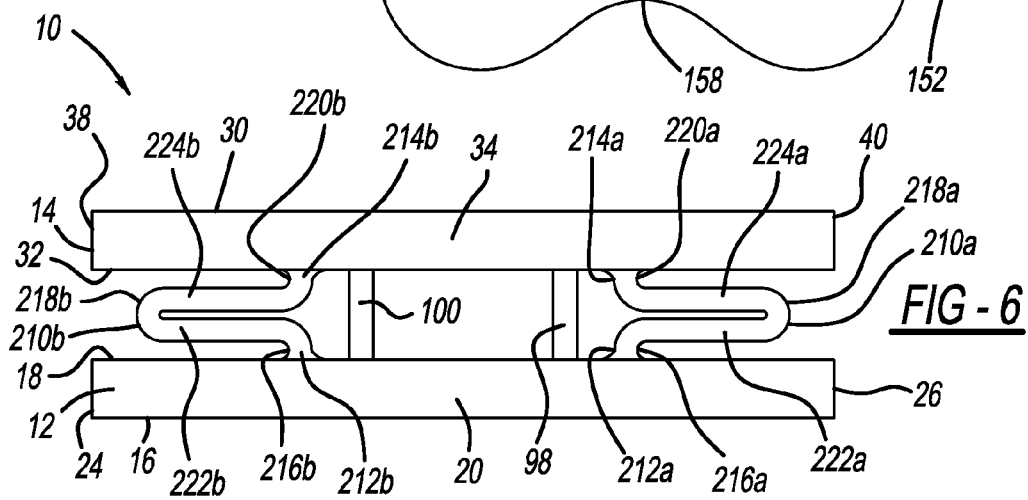
FIG. 6 is a side view of a trial joint spacer according to the present teachings.

The first plate 12 can be connected to the second plate 14 with any suitable coupling device, resilient member, or spring. Additional coupling devices of the joint spacer 10 will now be described. With reference to FIG. 6, an additional first coupling device is illustrated at reference numeral 210a. The coupling device 210a includes a first end 212a and a second end 214a. The first end 212a is coupled to the first plate 12 at the first inner surface 18. The second end 214a is coupled to the second plate 14 at the second inner surface 32. The first end 212a and the second end 214a are vertically aligned with one another in the superior/inferior direction.

The first coupling device 210a can be connected to the first plate 12 and the second plate 14 at the first end 212a and at the second end 214a respectively in any suitable manner. For example, the coupling device 210a can be integral with the first plate 12 and the second plate 14, or fastened to the first plate 12 at the first end 212a and fastened to the second plate 14 at the second end 214a in any suitable manner, such as by welding.

The first coupling device 210a extends from the first end 212a toward the second plate 14 and then curves about 90 degrees at first curve or hinge 216a in the direction of the lateral side 26. The first coupling device extends towards the lateral side 26 and then curves about 180 degrees back upon itself at second curved or folded portion 218a, which can be a hinge of the first coupling device 210a. From the second curve 218a, the first coupling device 210a turns towards the second plate 14 and then extends away from the lateral side 40. At third curved or hinged portion 220a, the first coupling device 210a turns about 90 degrees and extends to the second plate 14 where the first coupling device 50a is coupled to the second plate 14 at the second end 214a.

The first coupling device 210a thus includes a first elongated portion 222a and a second elongated portion 224a. The first elongated portion 222a extends between the first curve 216a and the second curve 218a. The second elongated portion 224a extends between the second curve 218a and the third curve 220a. The first elongated portion 222a extends generally parallel to the second elongated portion 224a.

The joint spacer 10 can include a plurality of coupling devices similar to the first coupling device 210a, such as a second coupling device 210b, as illustrated in FIG. 6. The first and second coupling devices 210a and 210b can be arranged at any suitable location about the joint spacer 10 and arranged in any suitable orientation. For example, the first and second coupling devices 210a and 210b can be arranged such that they extend outward towards the lateral sides 26/40 and the medial sides 24/38 respectively, as illustrated in FIG. 6. The first coupling device 210a and the second coupling device 210b can also be arranged such that they both extend towards the anterior sides 20/34, towards the posterior sides 22/36, or in opposite directions, such as with the first coupling device 210a extending towards the anterior sides 20/34, and the second device 210b extending towards the posterior sides 22/36. Any suitable number of the first and second coupling devices 210a and 210b can be included, such as four in generally the same orientation as illustrated in FIGS. 2 and 3 with respect to the coupling devices 50c-50f.

Figure 7:
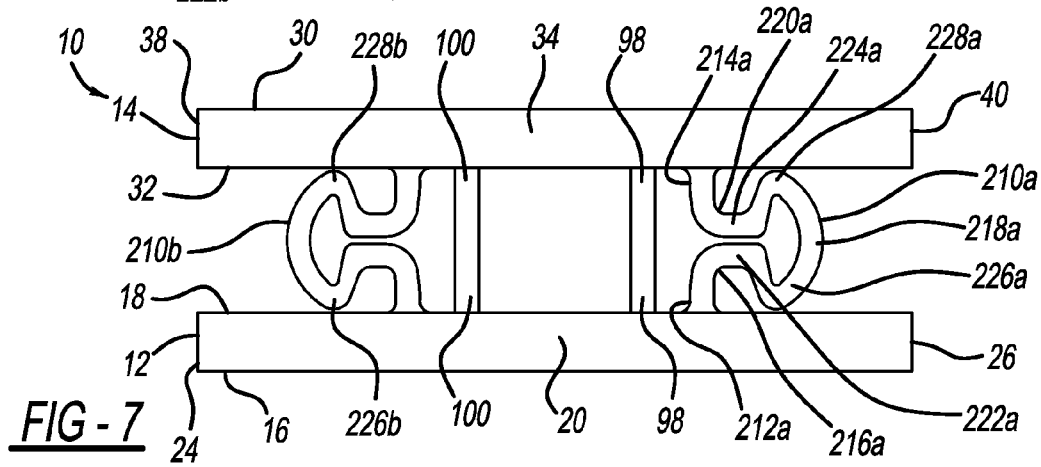
FIG. 7 is a side view of another trial joint spacer according to the present teachings.

With additional reference to FIG. 7, the first and second coupling devices 210a and 210b can be configured differently to increase the distance that the first and second coupling devices 210a and 210b can expand vertically in the inferior/superior direction, and thus increase the distance that the first plate 12 and the second plate 14 can expand, or be separated from one another. As illustrated in FIG. 7, the second curved portion 218a can be enlarged such that it extends from about the first plate 12 to about the second plate 14.

To provide the enlarged second curved portion 218a, the first coupling device 210a includes a fourth curved portion 226a and a fifth curved portion 228a, each of which can be hinges of the first coupling device 210a. The fourth curved portion 226a extends from the elongated portion 222a towards the first plate 12, then turns and extends away from the first plate 12 towards the second plate 14 to transition into the second curved portion 218a. Similarly, the fifth curved portion 228a extends from the second elongated portion 224a towards the second plate 14, and then turns away from the second plate 14 in order to transition into the second curved portion 218a. The second coupling device 210b includes curved portions 226b and 228b, which are generally similar to the curved portions 226a and 228a respectively.

Figure 8:
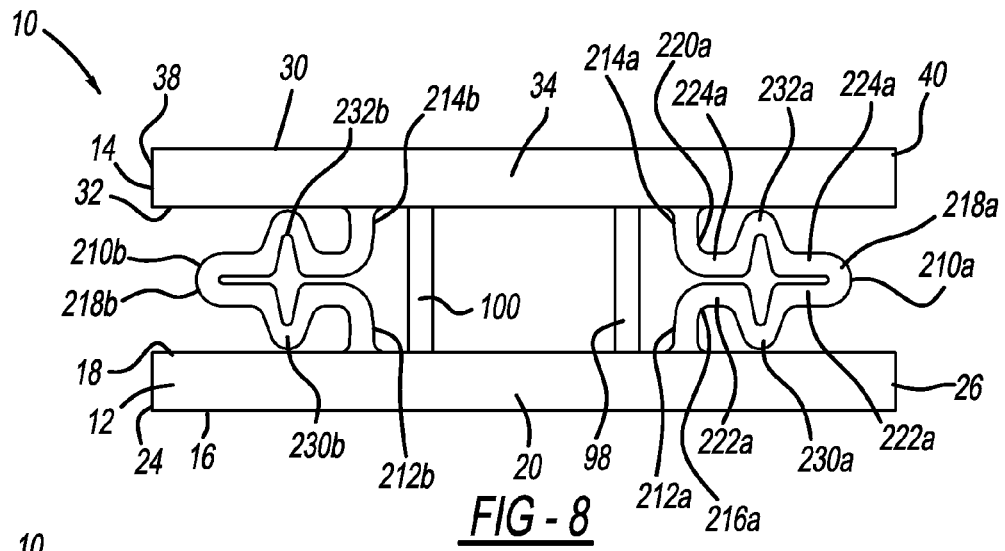
FIG. 8 is a side view of still another trial joint spacer according to the present teachings.

With additional reference to FIG. 8, the first coupling device 210a can include a first curved portion 230a along the elongated member 222a, and can include a second curved portion 232a along the second elongated member 224a. The first curved portion 230a extends to and away from the first plate 12, and the second curved portion 232a extends to and away from the second plate 14. Each of the curved portions 230a and 232a are generally U-shaped hinges and expand the range of extension of the first coupling device 210a. The second coupling device 210b can include curved portions 230b and 232b, which are similar to the curved portions 230a and 232b respectively.

Figure 9:
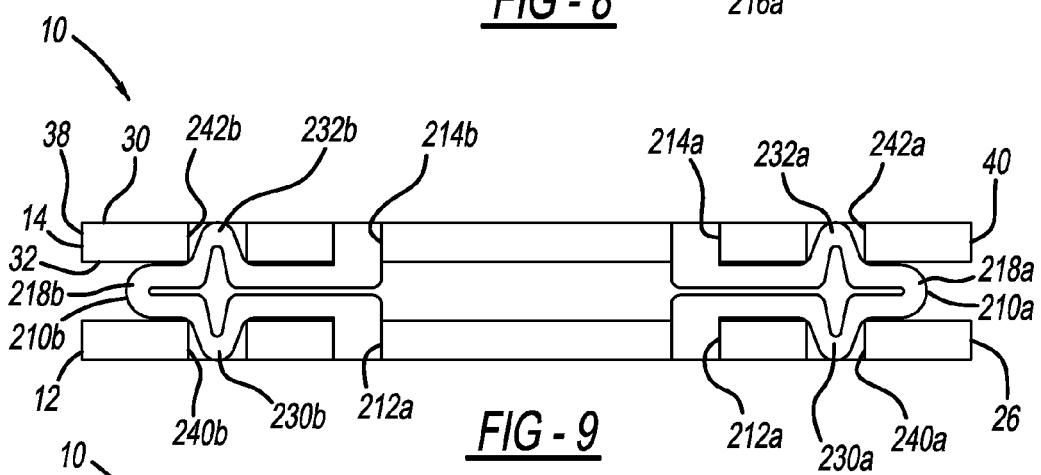
FIG. 9 is a cross-sectional view of another trial joint spacer according to the present teachings.

As illustrated in FIG. 8, the first and second coupling devices 210a and 210b are integrally formed with the first plate 12 and the second plate 14, and are thus monolithic therewith. The first and second coupling devices 210a and 210b can also be fastened to the first plate 12 and the second plate 14 in any suitable manner, such as by welding. This modular connection between the first coupling device 210a and the second coupling device 210b and the first and second plates 12 and 14 is illustrated in FIG. 9, for example. Any of the coupling devices described herein can be coupled to the first plate 12 and/or the second plate 14 with the modular connection.

With continued reference to FIG. 9, to accommodate the curved portions 230a, 232a, 230b, and 232b, the first plate 12 defines a receptacle 240a proximate to the lateral side 26 for receiving the curved portion 230 therein. The first plate 12 further defines a receptacle 240b proximate to the medial side 24 to receive the curved portion 230b of the second coupling device 210b therein. The second plate 14 defines a receptacle 242a proximate to the lateral side 40 to receive the curved portion 232a of the first coupling device 210a therein. The second plate 14 further defines a receptacle 242b proximate to the medial side 38 to receive the curved portion 232b therein. The receptacles 240a, 240b, 242a, and 242b allow the first and second plates 12 and 14 to be seated closer together.

Figure 10:
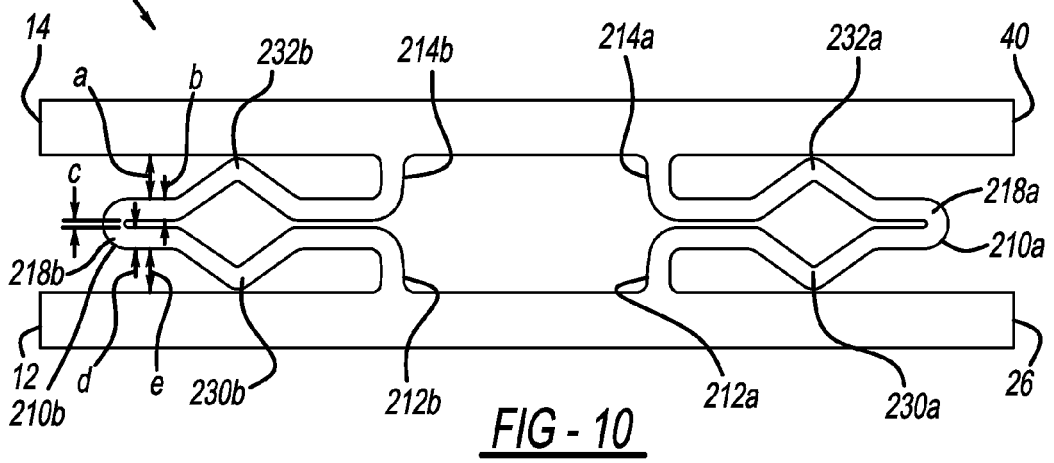
FIG. 10 is a side view of a coupling device of a trial joint spacer according to the present teachings.

With additional reference to FIG. 10, the curved portion 230a and the curved portion 232a can be less rounded as compared to that illustrated in FIG. 8 for example, and thus define an overall diamond shape. The curved portions 232a and 232b can each include curves or turns of about 90°. The folded portions 218a and 218b can be folded at angles of about 180°. Any other suitable angles of curves or turns can be provided as well.

The coupling devices described herein can have any suitable dimensions. For example and with reference to FIG. 10, the coupling device 210b can be spaced apart from the second plate 14 by a distance A of about 0.75 mm, and spaced apart from the first plate 12 by a distance E of about 0.75 mm. The coupling device 210b can be provided with a thickness of about 0.75 mm. at portions B and D. The portions of the coupling device 210b defining the curved portion 218b can be spaced apart by about 0.25 mm at portion C, for example. The first coupling device 210a of FIG. 10 can be sized in a similar manner.

With reference to FIG. 11, four coupling devices 210 may be included. The first coupling device 210a may be arranged proximate to the anterior sides 20/34 and the lateral sides 26/40. The second coupling device 210b can be arranged proximate to the anterior sides 20/34 and the medial sides 24/38. The third coupling device 210c can be arranged proximate to the lateral sides 26/40 and the posterior sides 22/36. A fourth coupling device 210d can be arranged proximate to the medial sides 24/38 and the posterior sides 22/36.

The third and fourth coupling devices 210c and 210d can be substantially similar or identical to any of the first and second coupling devices 210a and 210b. The coupling devices 210a through 210d can be arranged in any suitable orientation. For example, the coupling devices 210a-210d can extend in the medial to lateral direction or the anterior to posterior direction. All of the coupling devices 210a-210d can extend in the same direction and be oriented in a similar manner, or any suitable combination of opposing orientations can be provided. For example, the first and second coupling devices 210a and 210b can be arranged such that they extend towards the lateral side 26/40 and the medial side 24/38 respectively. The third and fourth coupling devices 210c and 210d can be arranged such that the coupling device 210c extends away from the lateral sides 26/40 and the coupling device 210d extends away from the medial sides 24/38. Any other suitable orientation of the coupling devices 210a-210d can be provided. As illustrated, the coupling devices 210a-210d extend in the medial to lateral direction and have a width in the anterior to posterior direction of about 1 mm. or more each.

With reference to FIG. 12, the first spacer insert 70a is illustrated as further including a first guide flange 84a and a second guide flange 86a. The first guide flange 84a extends from the first side surface 76a and the second guide flange 86a extends from the second side surface 78a. With additional reference to FIG. 13, the first plate 12 defines a first guide 250a with a shape corresponding to the shape of the first spacer insert 70a illustrated in FIG. 12. The guide 250a thus includes a first angled portion 252a and a second angled portion 254a configured to receive the first guide flange 84a and the second guide flange 86a respectively. Receipt of the first spacer insert 70a within the guide 250a prevents the first spacer insert 70a from sliding in the medial/lateral direction and thus retains the first spacer insert 70a at an optimal location between the first plate 12 and the second plate 14. Multiple spacer inserts can be seated atop the first spacer insert 70a, such as the second spacer insert 70b. The guide 250b has a shape that corresponds to guide flanges 84b and 86b of the second spacer insert 70b in order to retain the second spacer insert 70b at an optimal location between the first and second plates 12 and 14.

Figure 15:
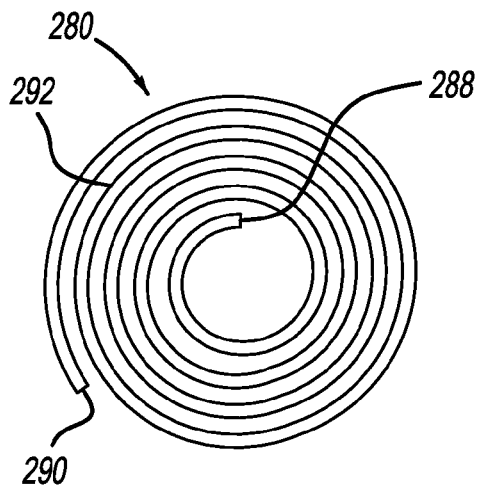
FIG. 15 is a plan view of the coupling device of FIG. 14.
Figure 16:
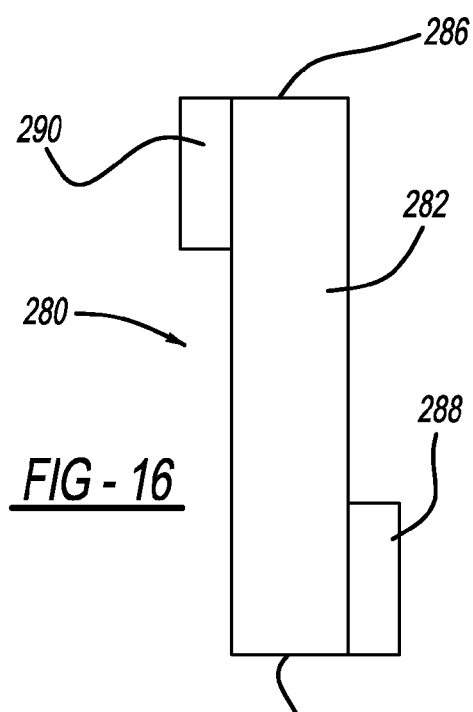
FIG. 16 is a plan, unwound view of the coupling device of FIG. 14.

With additional reference to FIGS. 14-16, an additional coupling device is illustrated at reference numeral 280. The coupling device 280 is generally formed of an elongated sheet 282, as illustrated in FIG. 16. The sheet 282 includes a first end 284 and a second end 286. At the first end 284 is a first flange 288 and at the second end 286 is a second flange 290. The first flange 288 is coupled to the first plate 12 in any suitable manner, such as by welding. The second flange 290 is connected to the second plate 14 in any suitable manner, such as by welding. The sheet 282 is rolled into a coil configuration 292 as illustrated in FIG. 15. The coil 292 is generally a resilient coil so as to bias the first plate 12 and the second plate 14 together. Multiple coupling devices 280 can be provided between the first and second plates 12 and 14 at any suitable position, such as one or more on the lateral side 26/40 and one or more on the medial side 24/38.

Figure 17:
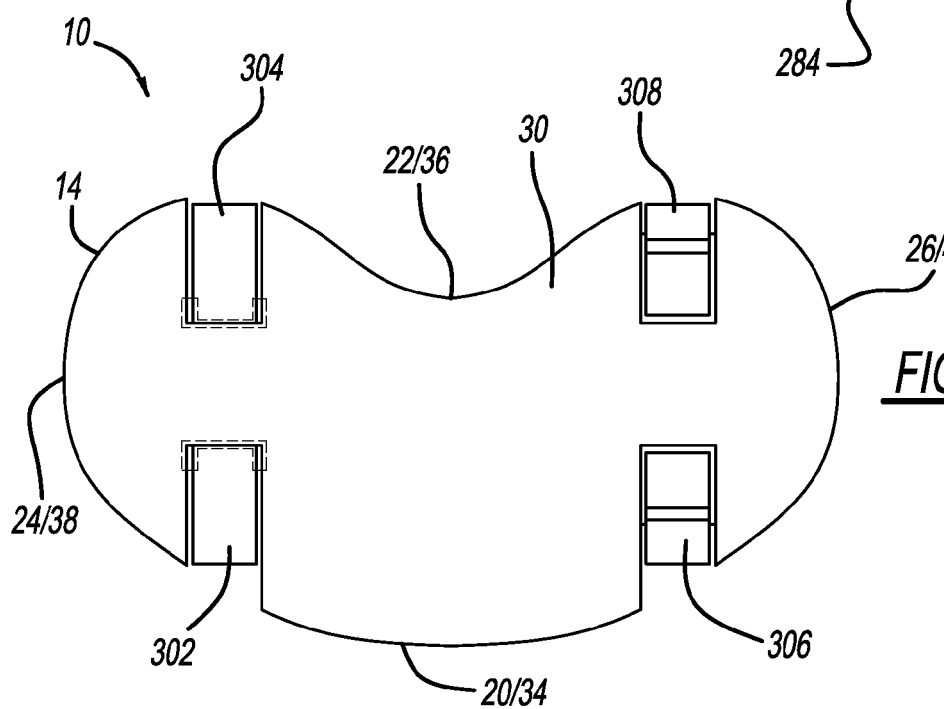
FIG. 17 is a plan view of another trial joint spacer according to the present teachings.
Figure 18:
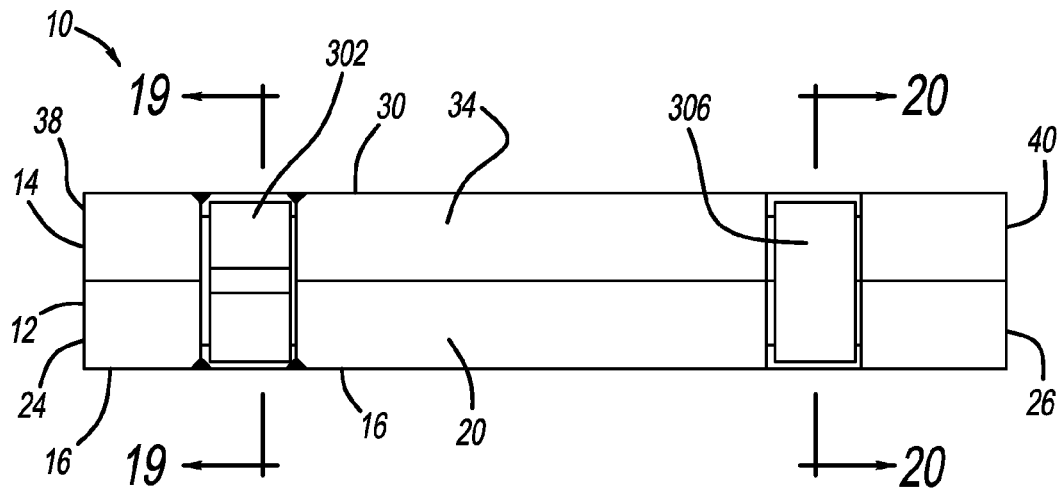
FIG. 18 is a side view of the trial joint spacer of FIG. 17.

With additional reference to FIGS. 17 and 18, additional coupling devices for coupling the first plate 12 and the second plate 14 together are illustrated. Coupling device 302 extends between the second bone facing surface 30 of the second plate 14 and the first bone facing surface 16 of the first plate 12 at the anterior sides 20 and 34. The coupling device 302 is at the medial sides 24 and 38. Coupling device 304 is also proximate to the medial sides 24 and 38, and extends between the second bone facing surface 30 of the second plate 14 and the first bone facing surface 16 of the first plate 12 at the posterior sides 22/36. The coupling device 306 extends from the second bone facing surface 30 to the first bone facing surface 16 at the posterior sides 22/36, and is proximate to the lateral sides 26 and 40. The coupling device 308 extends from the second bone facing surface 30 to the first bone facing surface 16 at the posterior sides 22/36, and is proximate to the lateral sides 26 and 40. The coupling devices 302 through 308 can be coupled to the first plate 12 and the second plate 14 in any suitable manner. For example, the coupling devices 302 and 304 can be welded at the second bone facing surface 30 and the first bone facing surface 16.

Figure 19:
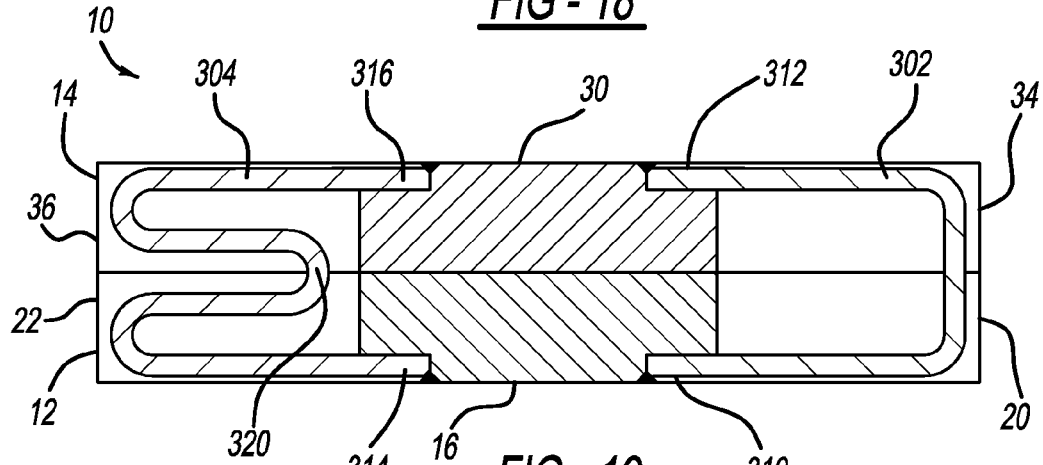
FIG. 19 is a cross-sectional view taken along line 19-19 of FIG. 18.

The coupling devices 302 and 304 are illustrated in FIG. 19 as including slightly different configurations or shapes, but it is contemplated that only one of the illustrated shapes will be used with a given joint spacer 10. The coupling device 302 generally includes a U-shape in cross-section, with a first end 310 welded at the first bone facing surface 16 and a second end 312 welded at the second bone facing surface 30. The coupling device 304 includes a first end 314 welded at the first bone facing surface 16 and a second end 316 welded at the second bone facing surface 30. The second coupling device 304 is shaped similar to the first coupling device 302, but includes a curved or folded hinge portion 320 approximately equidistant between the first end 314 and the second end 316. The curved portion 320 will allow the coupling device 304 to expand to a greater distance and the first coupling device 302 while requiring the same amount of space as the first coupling device 302 does.

With additional reference to FIG. 20, the coupling devices 306 and 308 will be described in detail. The coupling device 306 includes a first end 330, which is opposite to a second end 332. The first end 330 defines a flange inserted through the first bone facing surface 16 of the first plate 12 and seated beneath a tab 334 defined by the first plate 12 in order the couple the first end 330 to the first plate 12 just beneath the first bone facing surface 16. At the second end 332 is a similar flange recessed beneath a tab 336 at the second bone facing surface 30 of the second plate 14 to couple the second end 332 just beneath the second bone facing surface 30.

The coupling device 306 includes a first U-shaped curved portion 340 and a second U-shaped curved portion 342. The curved portions 340 and 342 are generally hinged portions of the coupling device 306. The curved portions 340 and 342 are generally arranged spaced apart and alongside to one another in the medial to lateral direction. Each of the first curved portion 340 and the second curved portion 342 are generally curved at 90 degrees. Because the first curved portion 340 and the second curved portion 342 are offset with respect to one another, they can extend further and allow the coupling device 306 to expand to a greater distance as compared to, for example, the coupling device 308.

Figure 20:
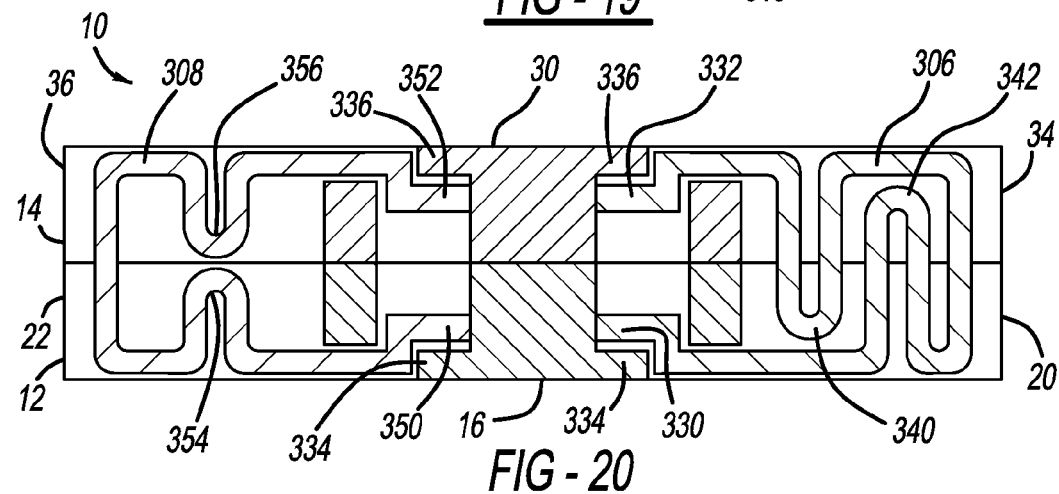
FIG. 20 is a cross-sectional view taken along line 20-20 of FIG. 18.

With continued reference to FIG. 20, the coupling device 308 includes a first end 350 and a second end 352, which is opposite to the first end 350. The coupling device 308 is coupled to the joint spacer 10 in a manner similar to that described above with respect to the coupling device 306. The coupling device 308 includes a first curved portion 354 and a second curved portion 356, which are respectively similar to the first curved portion 340 and the second curved portion 342, and are generally hinges of the coupling device 308. However, unlike the first curved portion 340 and the second curved portion 356, the first curved portion 354 is opposite to and aligned with the second curved portion 356.

Although the coupling devices 302-308 are illustrated as coupled to a single joint spacer 10, this is for ease of illustration and description only. In most applications, a single joint spacer 10 would include only the same type of coupling devices thereon. For example, a particular joint spacer 10 may include four of the coupling devices 302, another joint spacer 10 may include four of the coupling devices 304, another joint spacer 10 may include four coupling devices 306, and another joint spacer 10 may include four coupling devices 308.

Figure 21:
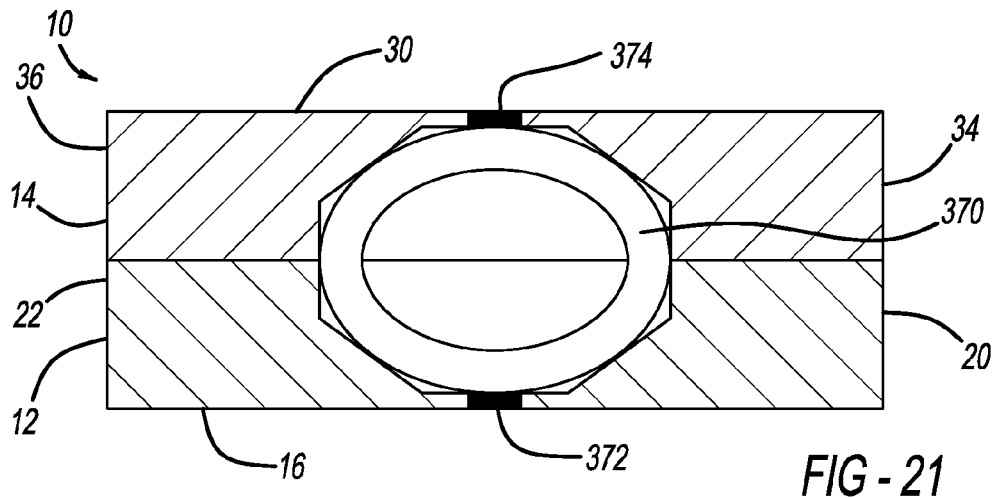
FIG. 21 is a cross-sectional view of yet another coupling device according to the present teachings for a trial joint spacer.
Figure 22:
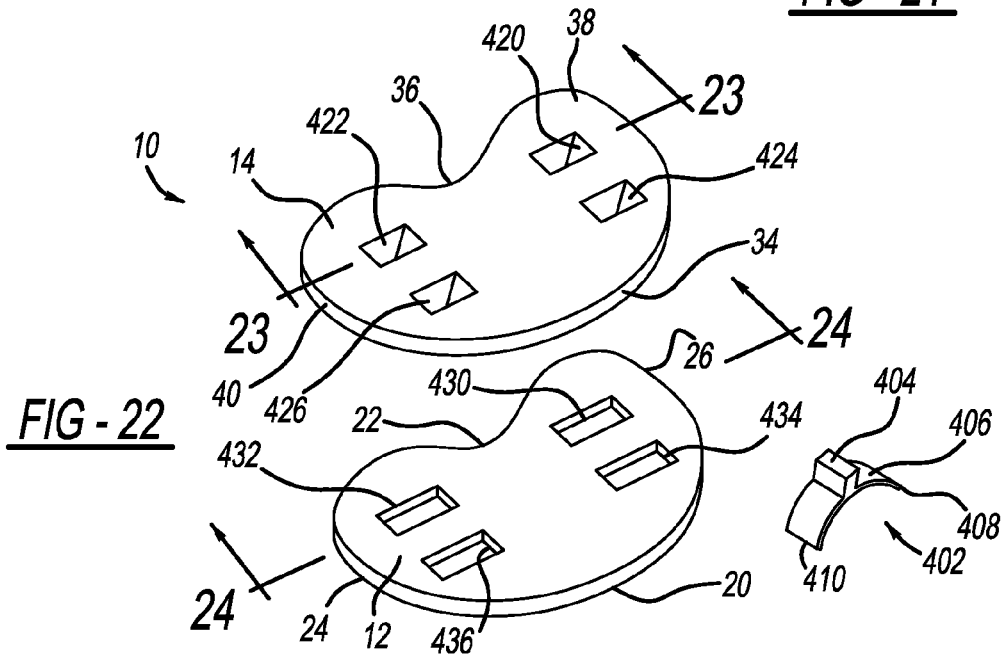
FIG. 22 is an additional trial joint spacer according to the present teachings.
Figure 23:
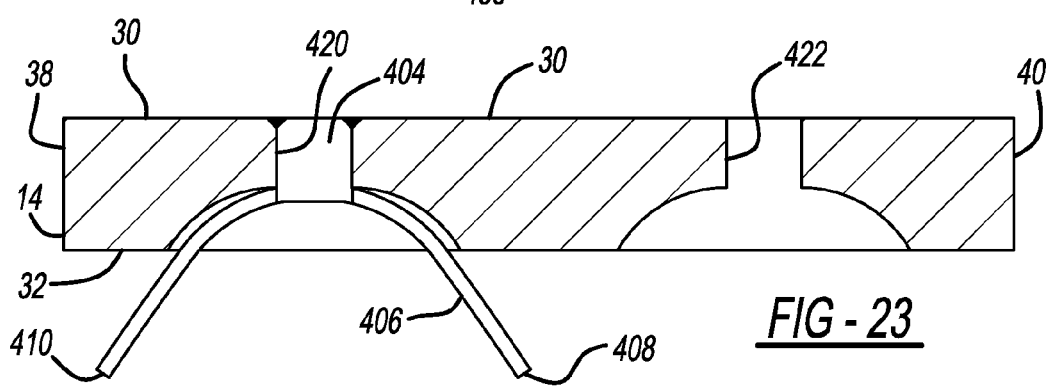
FIG. 23 is a cross-sectional view taken along line 23-23 of FIG. 22.

With additional reference to FIG. 21, a coupling device 370 is illustrated. The coupling device 370 is generally a tubular member having resilient properties, which thus acts as a spring. The coupling device 370 is coupled to the first plate 12 with a first coupling 372 and coupled to the second plate 14 with a second coupling 374. The first coupling 372 and the second coupling 374 can be any suitable couplings, such as welds. Any suitable number of coupling devices 370 can be included with the joint spacer 10 at any suitable location thereof, such as at any of the locations explained above with respect to the other coupling devices described herein. The coupling device 370 can also be arranged at any suitable orientation, such as extending in the medial/lateral direction or the anterior/posterior direction.

Figure 24:
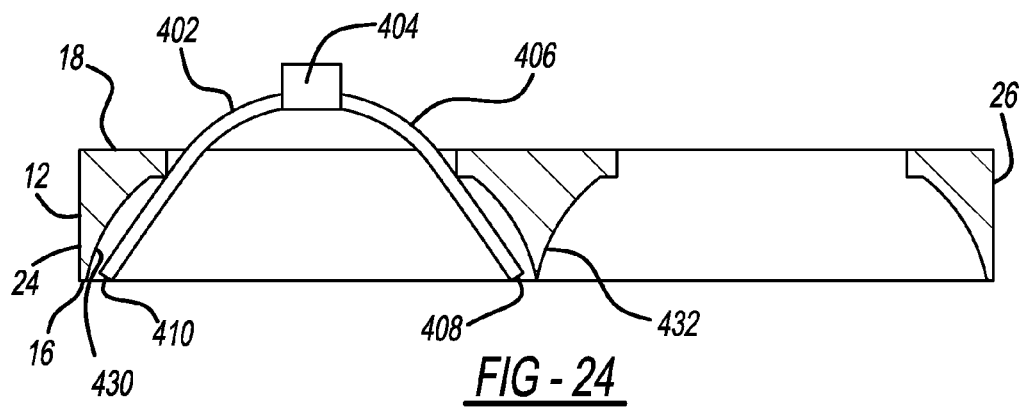
FIG. 24 is a cross-sectional view taken along line 24-24 of FIG. 22.
Figure 25:
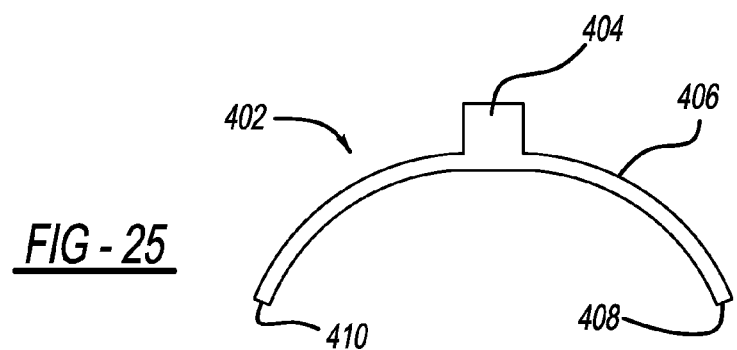
FIG. 25 is a side view of another coupling device according to the present teachings for the trial joint spacer of FIG. 22.

With additional reference to FIGS. 22-25, an additional coupling device is illustrated at reference numeral 402, with features thereof particularly visible in FIG. 25. The coupling device 402 includes a mounting member 404 and a resilient member 406 extending therefrom. A resilient member 406 includes a first end 408 and a second end 410.

The second plate 14 defines a plurality of apertures 420-426 arranged in any suitable location and at any suitable orientation. Each one of the apertures 420-426 is configured cooperate with a separate coupling device 402 by receiving a mounting member 404 therein. For example, the second plate 14 can define a first aperture 420, a second aperture 422, a third aperture 424, and a fourth aperture 426. With respect to the first aperture 420 for example, the mounting member 404 is seated therein and fastened within the first aperture 420 in any suitable manner, such as by welding. The resilient member 406 is arranged in a vertically aligned first receptacle 430 of the first plate 12.

As illustrated in FIG. 24, the first receptacle 430 is tapered inward from the first bone facing surface 16 towards the first inner surface 18. Therefore, as the second plate 14 is separated from the first plate 12, a resilient member 406 will flex inward such that the first end 408 and the second end 410 move closer together. Because the resilient member 406 is biased to be configured in an expanded position in which the first end 408 and the second end 410 are further apart, the resilient member 406 will resist movement out from within the first receptacle 430 and thus bias the second plate 14 against the first plate 12. The first plate 12 can include additional receptacles to receive additional resilient members 406, such as a second receptacle 432, a third receptacle 434, and a fourth receptacle 436. The receptacles 430-436 are generally aligned with one of the apertures 420-426 in order to receive a mounting member similar to mounting member 404 therein.

Figure 26:
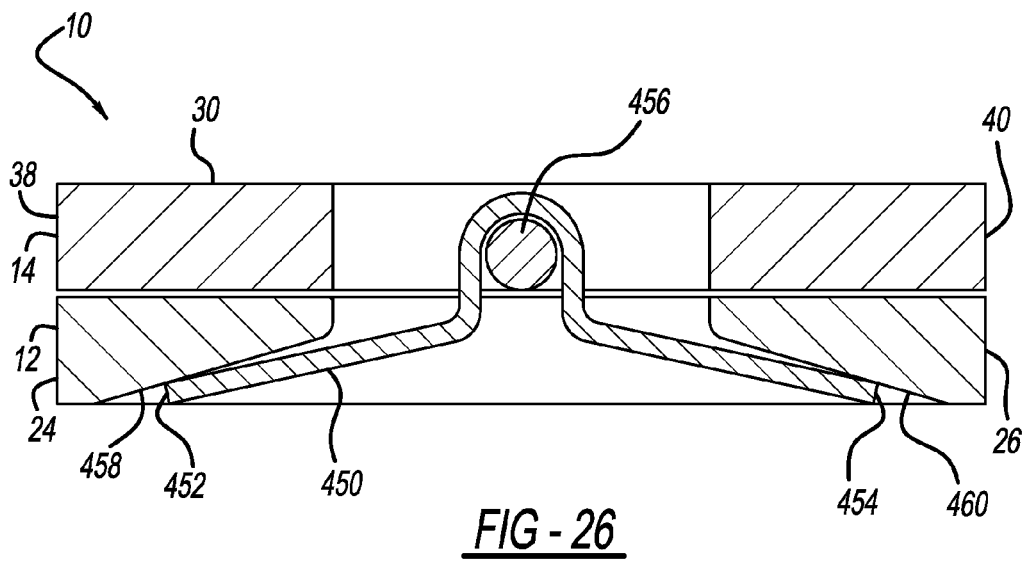
FIGS. 26-28 are cross-sectional views of another trial joint spacer according to the present teachings.
Figure 27:
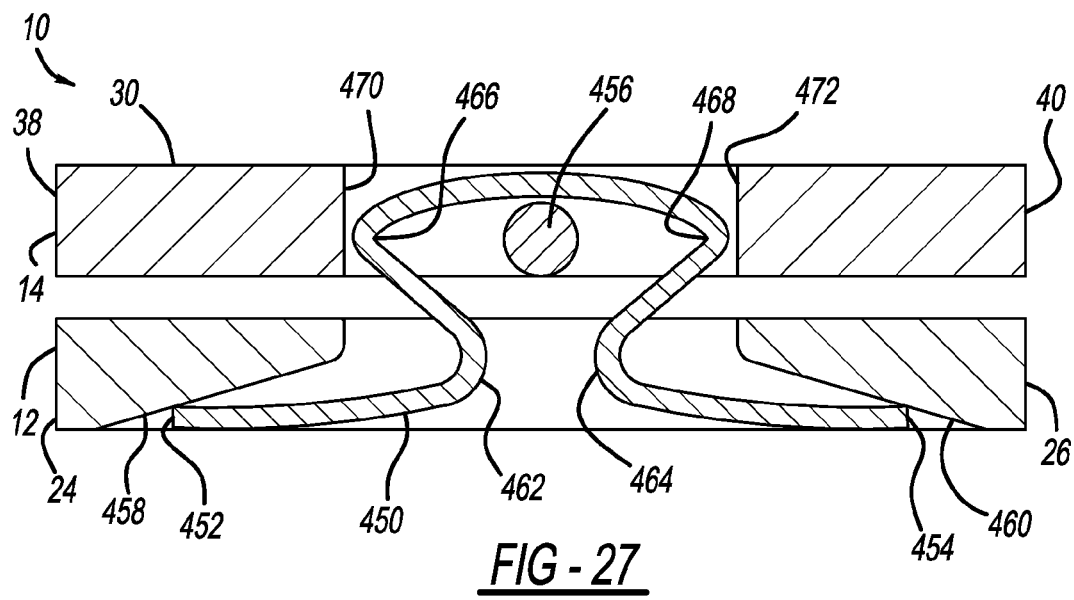
Figure 28:
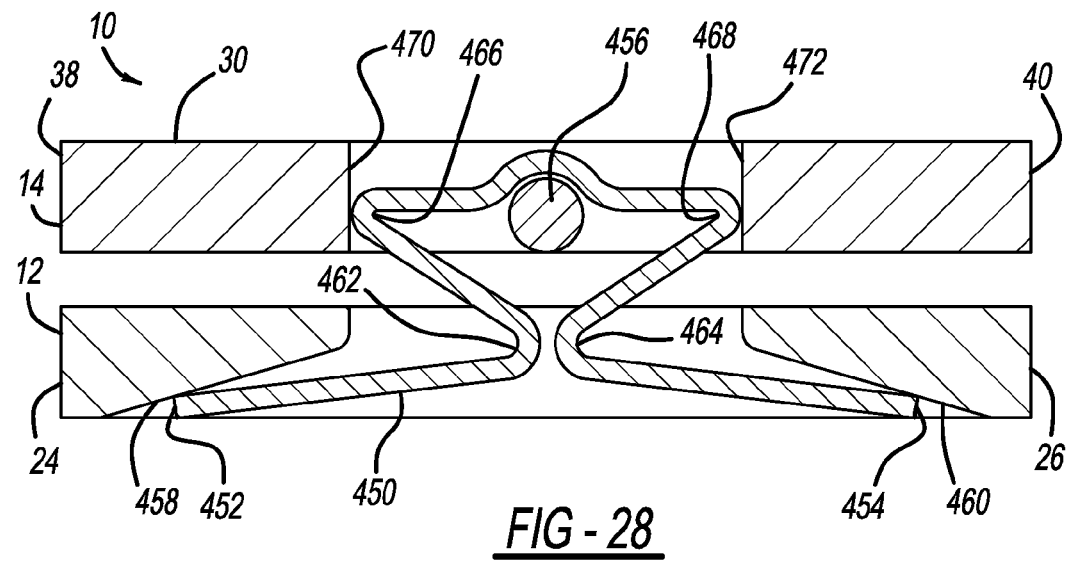

With additional reference to FIGS. 26-28, an additional coupling device is illustrated at reference numeral 450. The coupling device 450 is generally an elongated resilient member or leaf spring including a first end 452 and a second end 454, which is opposite to the first end 452. The coupling device 450 is seated over a dowel pin 456, or any other suitable supporting member, at the second plate 14. The first end 452 is arranged along a ramped surface 458 of the first plate 12 and the second end 454 is arranged along a ramped surface 460 of the first plate 12.

With additional reference to FIG. 27, as the second plate 14 is moved apart from the first plate 12, such as when spacer inserts 70 are inserted between the first plate 12 and the second plate 14, the coupling device 450 is pulled by the dowel pin 456 such that the first end 452 and the second end 454 slide along the ramped surfaces 458 and 460 respectively. The coupling device 450 will begin to deform such that a first curved portion 462 and a second curved portion 464 will be drawn toward one another so that the coupling device 450 nearly surrounds the dowel pin 456. Furthermore, curved portions 466 and 468 of the coupling device 450 will be formed and will extend outward from the dowel pin to contact opposing surfaces 470 and 472 of the second plate 14. The curved portions 462 and 464 will be drawn further together, such that the coupling device 450 will pull against the dowel pin 456 to bias the second plate 14 against the first plate 12. The coupling device 450 can be provided at any suitable location about the joint spacer 10 and any suitable number of the coupling devices 450 can be included. For example, four coupling devices 450 can be included evenly spaced apart about the joint spacer.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A joint spacer for a knee arthroplasty comprising:
a first plate including a femur facing surface, a first lateral side, a first medial side and a first inner surface;
a second plate including a tibia facing surface, a second lateral side, a second medial side and a second inner surface facing the first inner surface, wherein the first inner surface and the second inner surface define a receptacle having at least a medial portion located between the first and second medial sides and a lateral portion located between the first and second lateral sides;
a coupling device comprising a sheet rolled into a resilient coil configuration with a first end coupled to the first plate and a second end coupled to the second plate, the coupling device coupling the first plate and the second plate together; and
at least one spacer configured for insertion between the first plate and the second plate in both the medial and lateral portions of the receptacle to space the first plate and the second plate apart a distance corresponding to a desired interval between the tibia and femur.

2. The joint spacer of claim 1, further comprising a trial bearing plate configured to be mounted to the first plate or the second plate.

3. The joint spacer of claim 2, wherein the first plate or the second plate define a slot configured to receive a portion of the trial bearing plate therein; and wherein the trial bearing plate is a tibial trial bearing plate.

4. The joint spacer of claim 1, wherein the coupling device is welded to the first plate and the second plate.

5. The joint spacer of claim 1, wherein the coupling device includes a first anchor point at the femur facing surface of the first plate and a second anchor point at the tibia facing surface of the second plate.

6. A joint spacer for an orthopedic procedure comprising:
a first plate including a first bone facing surface and a first inner surface;
a second plate including a second bone facing surface and a second inner surface facing the first inner surface;
a coupling device that includes a leaf spring coupling the first plate and the second plate together; and
a spacer insert receiving portion of at least one of the first inner surface or the second inner surface configured to receive at least one spacer insert between the first plate and the second plate to space the first plate and the second plate apart a distance corresponding to an optimal interval between bones of a joint, wherein the leaf spring extends over a pin of the first plate, and first and second ends of the leaf spring are slidably seated on ramped surfaces of the second plate.

7. The joint spacer of claim 6, wherein the pin comprises a dowel pin.

8. The joint spacer of claim 6, wherein the leaf spring includes a first end arranged along a first ramped surface of the first plate and a second end arranged along a second ramped surface of the first plate.

9. The joint spacer of claim 8, wherein the coupling device is configured to be pulled by the pin such that the first end and the second end slide along the first and second ramped surfaces when the at least one spacer insert is inserted between the first plate and the second plate.

10. The joint spacer of claim 6, wherein the coupling device is configured to deform to nearly surround the pin when the at least one of the spacer insert is inserted between the first plate and the second plate.

11. The joint spacer of claim 6, wherein the coupling device includes a first curved portion and a second curved portion that are configured to be drawn toward one another when the at least one spacer insert is inserted between the first plate and the second plate.

12. The joint spacer of claim 6, wherein the coupling device includes a first curved portion and a second curved portion that are configured to extend outward from the dowel pin to contact opposing first and second surfaces and of the second plate.

13. The joint spacer of claim 6, wherein the coupling device comprises a plurality of coupling devices each spaced from one another.

14. The joint spacer of claim 1, wherein the coupling device comprises a plurality of coupling devices each spaced from one another.

15. A joint spacer for a knee arthroplasty comprising:
- a first plate including a femur facing surface, a first lateral side, a first medial side and a first inner surface;
- a second plate including a tibia facing surface, a second lateral side, a second medial side and a second inner surface facing the first inner surface, wherein the first inner surface and the second inner surface define a receptacle located between the first and second medial sides and the first and second lateral sides;
- a plurality of coupling devices including at least one medial coupling device disposed at the first and second medial sides and at least one lateral coupling device disposed at the first and second lateral sides, the medial and lateral coupling devices further defining the receptacle and coupling the first plate and the second plate together; and
- at least one spacer configured to insert between the first plate and the second plate in the receptacle between the at least the first and second coupling devices to space the first plate and the second plate apart a distance corresponding to an desired interval between the tibia and femur.

16. The joint spacer of claim 15, wherein the at least one medial coupling device disposed at the first and second medial sides comprises a first medial device disposed at a posterior side of one or both of the first plate and the second plate and a second medial coupling device disposed at an anterior side of one or both of the first plate and the second plate.

17. The joint spacer of claim 15, wherein the at least one lateral coupling device disposed at the first and second lateral sides comprises a first lateral coupling device disposed at a posterior side of one or both of the first plate and the second plate and a second lateral coupling device disposed at an anterior side of one or both of the first plate and the second plate.

18. The joint spacer of claim 15, wherein the medial and lateral coupling devices are welded at the tibia facing surface and the femur facing surface.

19. The joint spacer of claim 15, further comprising a trial bearing plate configured to be mounted to the first plate or the second plate.

20. The joint spacer of claim 19, wherein the first plate or the second plate define a slot configured to receive a portion of the trial bearing plate therein; and wherein the trial bearing plate is a tibial trial bearing plate.

21. The joint spacer of claim 15, wherein at least one of the first plate or the second plate defines a guide for receiving the at least one spacer insert.

22. The joint spacer of claim 15, further comprising a stop between the first plate and the second plate to maintain a minimum interval between the first plate and the second plate.

* * * * *